United States Patent [19]

Tsubokura et al.

[11] Patent Number: 5,229,281

[45] Date of Patent: Jul. 20, 1993

[54] **PROCESS FOR PRODUCTION OF OPTICALLY ACTIVE 3-METHYLADIPIC ACID FROM SQUALENE USING *CANDIDA LIPOLYTICA***

[75] Inventors: Akira Tsubokura, Kawasaki; Hisashi Yoneda; Takashi Kiyota, both of Yokohama, all of Japan

[73] Assignee: Nippon Oil Co., Ltd., Tokyo, Japan

[21] Appl. No.: 774,464

[22] Filed: Oct. 10, 1991

[30] Foreign Application Priority Data

Oct. 17, 1990 [JP] Japan ................................. 2-276389
Sep. 3, 1991 [JP] Japan ................................. 3-222835

[51] Int. Cl.$^5$ ............................. C12P 7/44; C12N 1/38
[52] U.S. Cl. .................................. 435/142; 435/244; 435/923
[58] Field of Search ............... 435/244, 142, 923, 244, 435/142, 923

[56] References Cited

U.S. PATENT DOCUMENTS 3,843,466 10/1974 Akabori et al. ................... 195/28 R

OTHER PUBLICATIONS

Santaniello E, J. Chem Soc Chem Commun 1984:803–4.

*Primary Examiner*—Douglas W. Robinson
*Assistant Examiner*—Sandra Saucier
*Attorney, Agent, or Firm*—Seed and Berry

[57] ABSTRACT

A process for the production of an optically active 3-methyladipic acid represented by the formula (I):

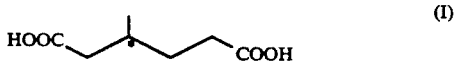

wherein the symbol * represents an asymmetric carbon atom, comprising the steps of culturing a microorganism belonging to the genus Candida and capable of producing the optically active 3-methyladipic acid in a medium containing squalene, to produce an optically active 3-methyladipic acid; and recovering the optically active 3-methyladipic acid from the cultured product.

4 Claims, 2 Drawing Sheets

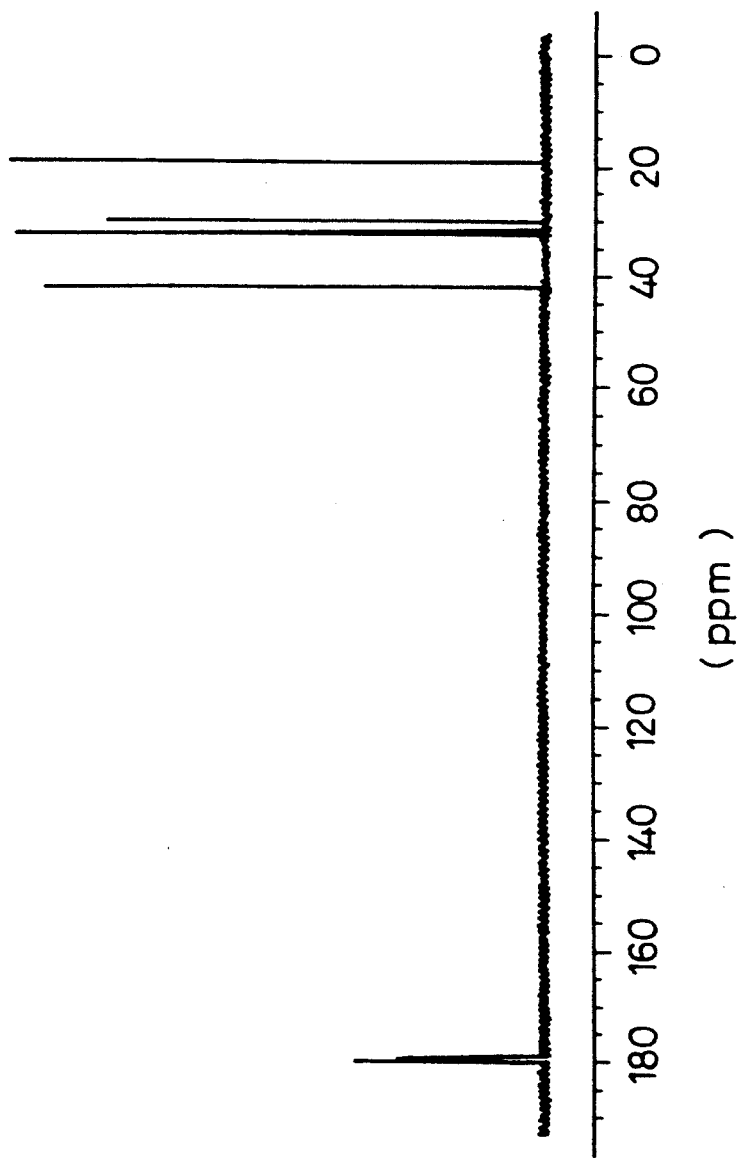

PROCESS FOR PRODUCTION OF OPTICALLY ACTIVE 3-METHYLADIPIC ACID FROM SQUALENE USING CANDIDA LIPOLYTICA

BACKGROUND OF THE INVENTION

1. Field of the Invention

The present invention relates to a process for the production of an optically active 3-methyladipic acid from squalene. The optically active 3-methyladipic acid produced by the present invention is a chiral compound having a methyl group on the asymmetric carbon atom, and is useful as a starting material for synthesis of pharmaceuticals, agrochemicals and other physiologically active substances, and as a starting material for liquid crystal polymers.

2. Description of the Related Art

Currently, as processes for the production of optically active 3-methyladipic acid, there are known a process wherein an optically active naturally occurring compound, (S)-(−)-citronellol is oxidated to form (S)-(−)-3-methyladipic acid (J. Chem. Soc. Commum., 803, 1984), and a process wherein an optically active naturally occurring compound, (R)-(+)-pulegone acid is oxidated to form (R)-(+)-3-methyladipic acid (Bull. Soc. Chim. Fr.[5]6, 1355, 1939), but the above processes are both disadvantageous from the industrial point of view in that they use an expensive optically active substance as a starting material, and further, provide a product having a low optical purity due to a recemization occurring during the oxidation.

SUMMARY OF THE INVENTION

Accordingly, the present invention provides a process for the production of an optically active 3-methyladipic acid having a very high optical purity. The optically active 3-methyladipic acid prepared by the present invention has an at least 95%, preferably at least 98%, and most preferably 100% optical purity.

Namely, the present invention provides a process for the production of an optically active 3-methyladipic acid represented by the formula (I):

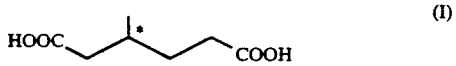

(I)

wherein the symbol * represents the asymmetric carbon atom, comprising culturing a microorganism belonging to the genus Candida and capable of converting squalene into an optically active 3-methyladipic acid, to thereby convert squalene to an optically active 3-methyladipic acid, and recovering the optically active 3-methyladipic acid.

BRIEF EXPLANATION OF THE DRAWINGS

FIG. 2 shows a $^{13}C$- nucleomagnetic resonance (NMR) spectrum of (S)-(−)-3-methyladipic acid obtained by the present process.

DESCRIPTION OF THE PREFERRED EMBODIMENTS

Figure 1:
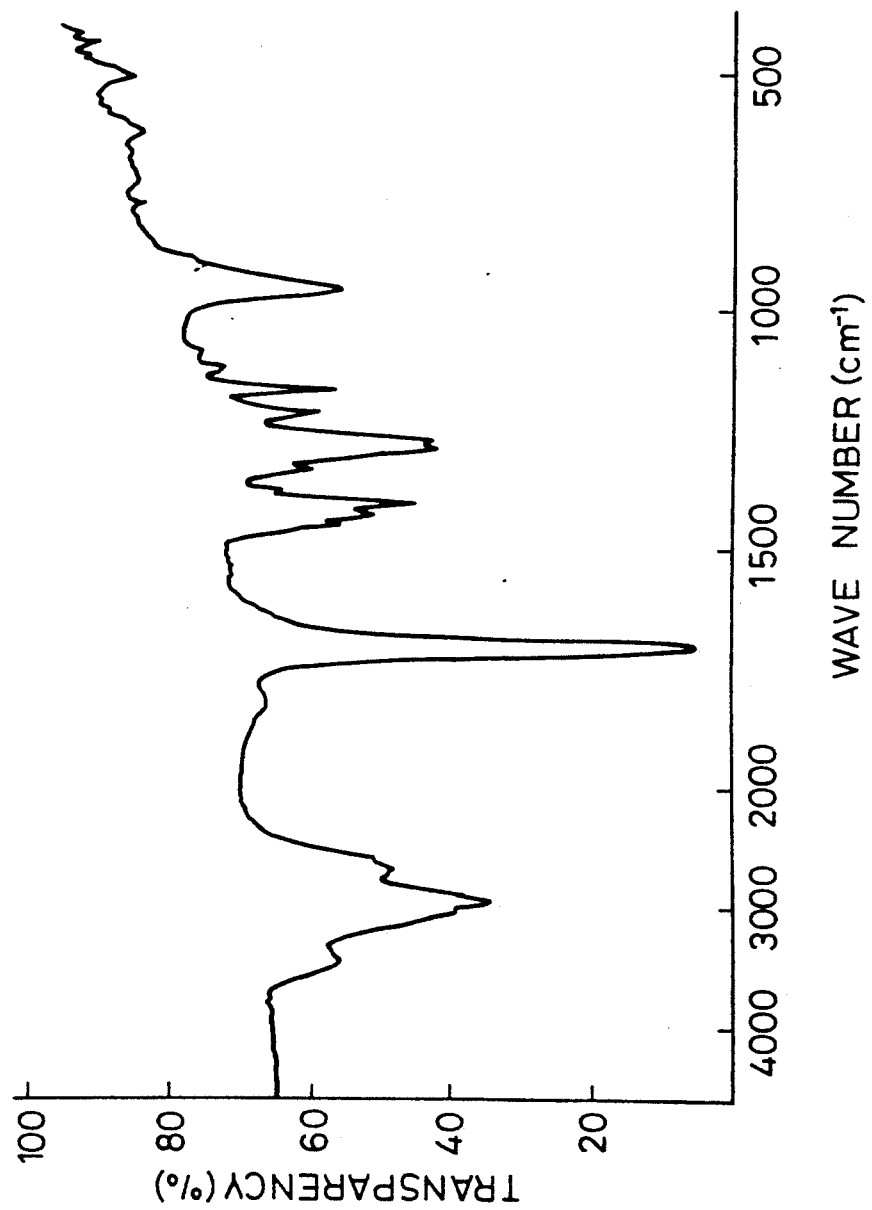
FIG. 1 shows an infrared absorption (IR) spectrum of (S)-(−)-3-methyladipic acid obtained by the present process.

Microorganisms belonging to the genus Candida and used in the present invention can be obtained, for example, by the following procedure. Namely, a naturally occurring source is added to a culture medium containing squalene as a sole carbon source, and culturing is carried out to isolate microorganisms capable of assimilating squalene as a carbon source from the culture.

As the culture medium, any conventional medium can be used as long as it contains squalene as a sole carbon source; i.e., contains components necessary for the growth of the microorganism, such as a nitrogen source, inorganic salts, and if necessary, other minor nutrients such as vitamins, amino acids, and nucleotides and the like. The squalene as a sole carbon source is contained in an amount of 0.1 to 100 g, preferably 1 to 10 g per liter.

As the nitrogen source, for example, potassium nitrate, ammonium nitrate, ammonium chloride, ammonium sulfate, ammonium phosphate, ammonia, urea and the like are used alone or in combination. The amount of nitrogen source used varies, depending on the nature of the nitrogen source, and is usually 0.1 to 10 g, preferably 1 to 3 g, per liter of the medium. As the inorganic salts, potassium phosphate, sodium phosphate, magnesium sulfate, ferric sulfate, ferric chloride, calcium chloride and the like are used alone or in combination. The amount of inorganic salts used varies, depending on the nature of the inorganic acid, and is usually 0.001 to 10 g, preferably 0.01 to 5 g, per liter.

If necessary, minor nutrients, such as vitamins, yeast extract, pepton, corn steep liquor and the like can be used alone or in combination. The amount added depends on the nature of additive, and is usually up to 10 g, for example 0.05 to 10 g, and preferably 0.1 to 5 g per liter. A pH value of a culture medium is 2 to 10, and preferably 3 to 6.

Further, an antibiotic, biocide or the like is preferably included in the medium, to allow a selective growth of a particular microorganism. For example, for a selective growth of yeast, streptomycin is added to the culture medium in an amount of 0.1 to 100 mg, preferably 10 to 50 mg/liter, to inhibit the growth of bacteria.

The sources from which microorganisms are isolated may be any naturally occurring materials, such as soil, sewerage, or spoiled fruit. The source is added to a medium in an amount of 1 to 100 g, preferably 30 to 50 g, per liter. The culture temperature is 15° to 80° C., preferably 20° to 35° C., and the culturing is carried out for 1 to 30 days, preferably 4 to 7 days, and then a part of the culture is inoculated to a fresh medium and the culturing is carried out for 1 to 30 days, preferably 4 to 7 days; this procedure is repeated 2 to 5 times. The culture is carried out under an aerobic condition provided by a conventional means such as aeration or stirring, or a combination thereof.

The growth of microorganisms is determined by a measurement of the turbidity or by a microscopical observation. Preferably, the isolation of microorganisms is carried out after the turbidity reaches $OD_{610}=0.1$ to 10, more preferably 0.2 to 1. For the isolation, a conventional isolation method such as a plate culture method is preferably used. The plate culture medium contains 0.1 to 10% agar and is, for example, a yeast extract/malt extract medium containing 2% agar (YM agar medium).

As an example of a microorganism isolated according to the above-mentioned procedure and able to be used for the present process, a yeast strain SQL349 is mentioned. This strain SQL349 was deposited with the Fermentation Research Institute Agency of Industrial Science and Technology, 1-3, Higashi 1-chome, Tsukuba-shi, Ibaraki-ken, Japan, as FERM P-11653 on Aug. 9, 1990, and transferred to an international deposition under the Budapest Treaty as FERM BP-3580 on Sep. 26, 1991.

The microorganism SQL349 has the following taxonomical properties.

| a. | Morphology | | | |
|---|---|---|---|---|
| | Vegetable cell: spherical-elliptic, proliferating by multi-poler budding | | | |
| | Liquid culture: forming precipitate and surface film layer (25° C., 3 days) | | | |
| | Pseudomycelium: formed (25° C., 3 days) | | | |
| | True mycelium: formed (25° C., 6 days) | | | |
| | Ascospore: not formed on Adams medium, Gorodkowa medium, malt medium, YM medium, V-8 medium, and a potato-dextrose medium | | | |
| b. | Physiological properties | | | |
| | (1) | Fermentation of sugars | | |
| | | Glucose | − | Sucrose | − |
| | | Maltose | − | Lactose | − |
| | | Raffinose | − | Galactose | − |
| | (2) | Assimilation of: | | |
| | | Nitrate | − | Inositol | − |
| | | Erythritol | + | Galactose | − |
| | | Glucose | + | Sucrose | − |
| | | Cellobiose | − | Trehalose | − |
| | | Maltose | − | Lactose | − |
| | | Raffinose | − | | |
| | (3) | Growth temperature | | |
| | | 25° C. | + | 30° C. | + |
| | | 37° C. | − | | |
| | (4) | DBB colorination reaction | − | |
| | (5) | Degradation of fat | + | |

According to the above result, the strain SQL349 was identified as *Candida lipolytica*. Note, *Candida lipolytica* is taxonomically the same as the imperfect generation of *Saccharomycopsis lipolytica* identified at the Institute of Fermentation Osaka (IFO) and the imperfect generation of *Yarrowia lipolytica* identified at the American Type Culture Collection (ATCC).

In addition to the above-mentioned microorganism, according to the present invention, for example, *Candida lipolytica* IFO 0746 (ATCC 20114), IFO 1209 (ATCC 8662), IFO 1542 (ATCC 20306), IFO 1632, IFO 1741, IFO 10073 (ATCC 48436), IFO 1742 (ATCC 9773), IFO 1195, IFO 1548 (ATCC 18942), IFO 1549 (ATCC 18945), IFO 1550 (18943), IFO 1746 ATCC 20237, ATCC 20255, ATCC 20362, ATCC 20363, ATCC 20460, ATCC 20461, ATCC 20496, ATCC 22421, ATCC 22422, ATCC 22423, ATCC 34922, ATCC 44601, ATCC 46330, ATCC 46482, ATCC 46483, ATCC 46484, and the like can be used, and among them, strains marked IFO can be obtained without limitation from the Institute of Fermentation Osaka, 17-85, Juso-honmachi 2-chome, Yodogawa-ku, Osaka 532, Japan; and strains marked ATCC can be obtained without limitation from the American Type Culture Collection (ATCC) 12301 Parklawn Drive, Rockville, Md. 20852, USA.

The medium used to produce 3-methyladipic acid according to the present process contains components necessary for the growth of a producer microorganism, i.e., a carbon source, nitrogen source, inorganic salts, and if necessary, minor components such as vitamins, amino acids, and nucleotides and the like. Although squalene can be used as a sole carbon source, if necessary sugars such as glucose or erythritol, hydrocarbons such as n-paraffins, or alcohols such as ethanol or propanol, etc., may be used. The amount of carbon source used varies, depending on the nature of carbon source, and is usually up to 100 g, for example, 0.1 to 100 g, preferably 0.5 to 10 g, per liter. As the nitrogen source, for example, potassium nitrate, ammonium nitrate, ammonium chloride, ammonium sulfate, ammonium phosphate, ammonia, urea and the like are used alone or in combination. The amount of nitrogen source varies, depending on the nature of the nitrogen source, and is usually 0.1 to 10 g, preferably 1 to 3 g, per liter of medium.

As the inorganic acids, potassium phosphate, sodium phosphate, magnesium sulfate, ferric sulfate, ferric chloride, calcium chloride and the like are used alone or in combination. The amount of inorganic salts depends on the nature of the inorganic salt, and is usually 0.001 to 10 g, preferably 0.01 to 5 g, per liter. If necessary, vitamins, nucleotides, yeast extract, pepton, corn steep liquor and the like are used alone or in combination. The amount of the additive depends on the nature of the additive, and is usually up to 10 g, for example, 0.05 to 10 g, preferably 0.1 to 5 g, per liter.

A pH value of a medium is usually adjusted to 2 to 11, preferably 3 to 6. If the pH value of the medium is lowered during the culturing, the pH value is controlled if necessary by adding an alkali such as an NaOH aqueous solution. In addition to the above-mentioned medium, other conventional media such as a bouillon medium, yeast extract/malt extract medium (YM medium) and the like may be used.

As a precursor of the 3-methyladipic acid, squalene is added to a culture medium. The squalene may be added to the medium before the onset of culturing, or may be added continuously or periodically during the culturing. The total amount of squalene used is, for example, 0.1 to 100 g, preferably 2 to 20 g, per liter.

To produce a large amount of the desired product, a large scale culture is necessary, and accordingly, an inoculum culture is preferably prepared prior to the production culture. For the inoculum culture the same medium as described above the for production culture can be used, except that squalene is not necessary in the inoculum culture medium.

For the inoculum culture and production culture (main culture), culturing is carried out at 15° to 80° C., preferably 20° to 35° C., for 1 to 20 days, preferably 2 to 5 days, with shaking, stirring, agitation and/or aeration.

According to another embodiment of the present invention, once a producer microorganism is cultured, and the cultured cells brought into contact with squalene in an aqueous medium such as phosphate buffer under an aerobic condition, for example, under the same condition as that used for the culturing as described above, to produce the desired product, i.e., 3-methyladipic acid.

The method of recovering the desired product from a cultured broth or reaction mixture is not critical. For example, first a culture broth or reaction mixture is adjusted to a pH of 1 to 6, preferably a pH of 1 to 3, and then extracted with a solvent to obtain an extract containing the desired product, i.e., 3-methyladipic acid.

Any solvent which dissolves the desired product, for example, an organic solvent such as carbon tetrachloride, trichloroethylene, toluene, benzene, dichloromethane, chloroform, diethyl ether or ethyl acetate, may be used, but preferably dichloromethane, chloroform, diethyl ether or ethyl acetate is used.

To isolate and purify the desired product from the extract, conventional procedures such as adsorption, elution, distillation and the like may be used. For example, an extract is evaporated to remove a solvent, and form the resulting residue, the desired product is purified by adsorption chromatography using silica gel, active carbon, stylene-divinylbenzene copolymer resin or the like; and ion exchange chromatography using strong anion-exchange resin; weak anion-exchange resin or the like.

Alternatively, the products can be methyl-esterified by a conventional methyl-esterification method, for example, by refluxing with methanol in the presence of an acid catalyst, and the resulting ester mixture distilled to isolate 3-methyladipate methyl ester.

In the present invention, the identification and determination of the optical purity for the optically active 3-methyladipic acid were carried out as follows. The confirmation of the desired product 3-methyladipic acid was carried out by IR spectrum, $^1$H-NMR spectrum, $^{13}$C-NMR spectrum, and mass spectrum.

The absolute configuration and optical purity of the present compound were determined by a comparison of a specific rotation of the present compound with that described in literature, and a $^{13}$C-NMR spectrum analysis of a diastereomer of the present compound with L-menthol. Namely, the absolute configuration and optical purity of the product were obtained by comparing a specific rotation thereof with a specific rotation of (R)-(+)-3-methyladipic acid, $[\alpha]^{22}_D = +8.6°$ (c=5.0 g/100 ml, H$_2$O) described in the literature (Am. Soc. 69, 2568, 1947). Further, the product was reacted with L-menthol in the presence of p-toluenesulfonic acid to synthesize diastereomer, and the $^{13}$C-NMR spectrum thereof was then measured. Next, the optical purity was calculated from a ratio of signal areas of a carbon atom at the 2-position of the R-form and S-form of the 3-methyladipic acid moiety.

The present compound has carboxyl groups, and therefore, can form salts, for example, salts of alkaline metals such as lithium, sodium and potassium, alkaline earth metals such as calcium and magnesium, and ammonium, and the like. These salts can be obtained according to a conventional procedure from free compound. For example, a free compound can be neutralized with an appropriate base to obtain a corresponding salt.

Since the present compound has carboxyl groups, it can be converted to an aldehyde or alcohol by reducing same with, for example, lithium alminium hydride.

Therefore, according to the present invention, an optically active, highly pure 3-methyladipic acid can be produced.

EXAMPLES

Next, the present invention is explained in more detail with reference to Examples.

EXAMPLE 1

First, 50 ml each of the medium shown in Table 1 was put into 500 ml-Sakaguchi flasks and autoclaved at 121° C. for 20 minutes, to the medium was added 1 g of a soil sample (from Miura, Kanagawa, Japan), and then shaking culture was carried out at 30° C. for 5 days. Among these cultures, those in which microbial growth was observed were selected, a portion of the culture was plated on YM agar medium shown in Table 2, and a strain SQL349 (FERM BP-3580) was isolated.

This strain was cultured in YM liquid medium at 30° C. for 24 hours, with shaking, and a portion of the culture broth was inoculated into 50 ml of the medium having the composition shown in Table 1, at an inoculum ratio of 1% by volume, and culturing was carried out at 30° C. for 4 days. The culture broth was adjusted to pH of 2 with hydrochloric acid, and extracted with diethyl ether, and after phase separation, the organic phase was dried on anhydrous sodium sulfate, and the solvent then distilled off. The resulting solid residue was applied to a silica gel column, and then stepwise eluted with hexane/diethyl ether (100:10), hexane/diethyl ether (80:20), and hexane/diethyl ether (60:40), in this order.

Fractions of hexane/diethyl ether (60:40) were combined, the solvent was distilled off, and the resulting residue was adsorbed on a column containing HP-2MG resin (Mitsubishi Chemicals, Japan) and eluted with water/methanol (100:10) to obtain a fraction containing the desired compound (S)-(−)-3-methyladipic acid, which was obtained in the form of a white solid in an amount of 46 mg per liter of culture broth.

This compound was confirmed to be 3-methyladipic acid by IR spectrum, $^1$H-NMR spectrum, $^{13}$C-NMR spectrum and MASS spectrum. IR spectrum and $^{13}$C-NMR spectrum of the resulting 3-methyladipic acid are shown in FIGS. 1 and 2 respectively.

The absolute configuration and optical purity of the obtained compound were determined by a comparison of specific rotation thereof with a reported value, and a $^{13}$C-NMR spectrum analysis of a diastereomer of the product with L-menthol. Namely, a specific rotation of the product $[\alpha]^{22}_D = -8.9°$ (c=5.0 g/100 ml, H$_2$O) was compared with a reported value $[\alpha]^{22}_D = +8.6°$ (c=5.0 g/100 ml, H$_2$O) of (R)-(+)-3-methyladipic acid, and the configuration and optical purity of the product were determined as S-form and 100% respectively.

Further, the product was reacted with L-menthol in the presence of p-toluenesulfonic acid, to synthesize a diastereomer, and the $^{13}$C-NMR spectrum thereof was obtained. The enantiomer excess obtained from a ration of signal areas of carbon atom at a 2-position of the R-form and S-form of 3-methyladipic acid was at least 98% e.e.

TABLE 1

| Composition | Amount added |
| --- | --- |
| Squalene | 2.0 g/L |
| NH$_4$NO$_3$ | 2.5 g/L |
| KH$_2$PO$_4$ | 1.5 g/L |
| Na$_2$HPO$_4$ | 1.5 g/L |
| MgSO$_4$.7H$_2$O | 0.5 g/L |
| FeSO$_4$.7H$_2$O | 0.01 g/L |
| CaCl$_2$.2H$_2$O | 0.01 g/L |
| Yeast extract | 0.2 g/L |
| pH 5.0 | |

TABLE 2

| Composition | Amount added |
| --- | --- |
| Yeast extract | 3.0 g/L |
| Malt extract | 3.0 g/L |
| Pepton | 5.0 g/L |
| Glucose | 10.0 g/L |
| Agar | 20.0 g/L |
| pH 6.0 | |

EXAMPLE 2

Strain SQL349 (FERM BP-3580) was cultured in a YM liquid medium at 30° C. for 16 hours, with shaking, and the culture broth was inoculated to 3 l of a medium in a 5 l jar fermenter. The medium had a composition shown in Table 1 but contained 10.0 g/l squalene and 1.0 g/l glucose as carbon sources. The culturing was carried out at 30° C., 500 rpm and 0.8 VVM aeration for 64 hours, and the produced (S)-(−)-3-methyladipic acid was purified according to the same procedure as described in Example 1 to obtain (S)-(−)-3-methyladipic acid at a yield of 0.85 g per liter of culture broth.

The product was confirmed to be (S)-(−)-3-methyladipic acid by IR spectrum, $^1$H-NMR spectrum, $^{13}$C-NMR spectrum, MASS spectrum, specific rotation, and $^{13}$C-NMR of diastereomer with L-menthol, and the optical purity was at least 98%.

EXAMPLE 3

A strain SQL349 (FERM BP-3580) was cultured in 10 ml of a YM medium at 30° C. for 72 hours, and the culture was centrifuged to obtain cultured cells. The cells were washed with 0.1M phosphate buffer (pH 7) and suspended in 10 ml of the same buffer, 10 mg of glucose and 20 mg of squalene were added therein, and the mixture was shaken at 30° C. for 48 hours. The product (S)-(−)-3-methyladipic acid was purified according to the same procedure as described in Example 1, and as a result, (S)-(−)-3-methyladipic acid was obtained at a yield of 69 mg/l of reaction mixture.

The product was confirmed to be (S)-(−)-3-methyladipic acid by IR spectrum, $^1$H-NMR spectrum, $^{13}$C-NMR spectrum, MASS spectrum, specific rotation, and $^{13}$C-NMR spectrum of diastereomer with L-menthol, and the optical purity was at least 98%.

EXAMPLE 4

Microbial strains shown in Table 3 were separately cultured according to the same method as described in Example 2, to produce optically active 3-methyladipic acid. The products thereof were purified and the optical activity determined as described in Example 1.

TABLE 3

| Strain | Culture time (hr) | Amount of 3-methyladipic acid produced (g/L) | Steric Configuration | Optical purity (%) |
| --- | --- | --- | --- | --- |
| IFO 10073 | 72 | 0.7 | S | >99 |
| IFO 1209 | 99 | 0.6 | S | >99 |
| IFO 1741 | 90 | 1.0 | S | >99 |
| IFO 1742 | 163 | 0.5 | S | >99 |
| IFO 0746 | 100 | 0.1 | S | >99 |

We claim:

1. A process for product of (S)-(−)-3-methyladipic acid represented by the formula (I):

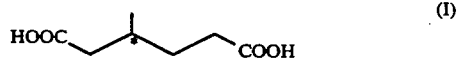

wherein the symbol * represents an asymmetric carbon atom, comprising the steps of:
culturing a microorganism belong to *Candida lipolytica* and capable of producing (S)-(−)-3-methyladipic acid in a medium containing squalene as the substrate for the product of said (S)-(−)-3-methyladipic acid, to product (S)-(−)-3-methyladipic acid; and
recovering the (S)-(−)-3-methyladipic acid from the culture product.

2. A process according to claim 1 wherein the *Candida lipolytica* is of a strain selected from the group consisting of *Candida lipolytica* SQL349 (FERM BP-3580), IFO 0746 (ATCC 20114), IFO 1209 (ATCC 8662), IFO 1542 (ATCC 20306), IFO 1632, IFO 1741, IFO 10073 (ATCC 48436), IFO 1742 (ATCC 9773), IFO 1195, IFO 1548 (ATCC 18942), IFO 1549 (ATCC 18945), IFO 1550 (ATCC 18943), IFO 1746, ATCC 20237, ATCC 20255, ATCC 20362, ATCC 20363, ATCC 20460, ATCC 20461, ATCC 20496, ATCC 22421, ATCC 22422, ATCC 22423, ATCC 34922, ATCC 44601, ATCC 46330, ATCC 46482, ATCC 46483, AND ATCC 46484.

3. A process according to claim 1 wherein the optical purity of the (S)-(−)-3-methyladipic acid is at least 95%.

4. A process according to claim 1 wherein the optical purity of the (S)-(−)-3-methyladipic acid is at least 98%.

* * * * *

UNITED STATES PATENT AND TRADEMARK OFFICE
CERTIFICATE OF CORRECTION

PATENT NO.  :  5,229,281
DATED       :  July 20, 1993
INVENTOR(S) :  Akira Tsubokura et al.

It is certified that error appears in the above-identified patent and that said Letters Patent is hereby corrected as shown below:

In column 8, claim 1, line 13, please delete "product" and substitute therefor --production--.

In column 8, claim 1, line 22, please delete "belong" and substitute therefor --belonging--.

In column 8, claim 1, line 25, please delete "product" and substitute therefor --production--.

In column 8, claim 1, line 26, please delete "product" and substitute therefor --produce--.

In column 8, claim 1, line 29, please delete "culture" and substitute therefor --cultured--.

Signed and Sealed this

Fifteenth Day of March, 1994

Attest:

BRUCE LEHMAN

Attesting Officer    Commissioner of Patents and Trademarks